(12) United States Patent
Shanbhag et al.

(10) Patent No.: US 11,605,455 B2
(45) Date of Patent: Mar. 14, 2023

(54) SYSTEMS AND METHODS FOR PREDICTING OUTCOMES USING RAW DATA

(71) Applicant: General Electric Company, Schenectady, NY (US)

(72) Inventors: Dattesh Dayanand Shanbhag, Bangalore (IN); Hariharan Ravishankar, Bangalore (IN); Rahul Venkataramani, Bangalore (IN)

(73) Assignee: GE Precision Healthcare LLC, Wauwatosa, WI (US)

( * ) Notice: Subject to any disclaimer, the term of this patent is extended or adjusted under 35 U.S.C. 154(b) by 48 days.

(21) Appl. No.: 16/722,409

(22) Filed: Dec. 20, 2019

(65) Prior Publication Data
US 2020/0203004 A1  Jun. 25, 2020

(51) Int. Cl.
*G16H 30/40* (2018.01)
*G06T 7/00* (2017.01)
(Continued)

(52) U.S. Cl.
CPC ............... *G16H 30/40* (2018.01); *G06N 3/08* (2013.01); *G06N 5/046* (2013.01); *G06N 20/00* (2019.01);
(Continued)

(58) Field of Classification Search
CPC .......... G06N 20/00; G06N 3/006; G06N 3/08; G06N 5/003; G06N 5/022; G06N 5/025; G06N 5/046
(Continued)

(56) References Cited

U.S. PATENT DOCUMENTS 10,074,038 B2    9/2018  Hsieh et al.
2013/0039549 A1*  2/2013  Muller ................. G01R 33/543
                                                 382/128
(Continued)

FOREIGN PATENT DOCUMENTS

CN    102622749 B    7/2014
CN    107067395 A    8/2017
(Continued)

OTHER PUBLICATIONS

Costafreda, Sergi G., et al.; "Automated Hippocampal Shape Analysis Predicts the Onset of Dementia in Mild Cognitive Impairment", NeuroImage, vol. 56, Issue: 1, pp. 212-219, May 1, 2011.
(Continued)

*Primary Examiner* — Ajibola A Akinyemi
(74) *Attorney, Agent, or Firm* — Fletcher Yoder P.C.

(57) ABSTRACT

The subject matter discussed herein relates to systems and methods for generating a clinical outcome based on creating a task-specific model associated with processing raw image (s). In one such example, input raw data is acquired using an imaging system, a selection input corresponding to a clinical task is received, and a task-specific model corresponding to the clinical task is retrieved. Using the task-specific model, the raw data is mapped onto an application specific manifold. Based on the mapping of the raw data onto the application specific manifold the clinical outcome is generated, and subsequently providing the clinical outcome for review.

23 Claims, 6 Drawing Sheets

(51) Int. Cl.
*G06N 3/08* (2023.01)
*G06N 20/00* (2019.01)
*G06N 5/046* (2023.01)

(52) U.S. Cl.
CPC .. *G06T 7/0012* (2013.01); *G06T 2207/10088* (2013.01); *G06T 2207/20081* (2013.01); *G06T 2207/20084* (2013.01)

(58) Field of Classification Search
USPC ........................................................ 382/128
See application file for complete search history.

(56) References Cited

U.S. PATENT DOCUMENTS

| | | | |
|---|---|---|---|
| 2014/0379379 A1* | 12/2014 | Janevski | G16H 50/20 705/3 |
| 2018/0182096 A1 | 6/2018 | Grady et al. | |
| 2019/0114547 A1* | 4/2019 | Jaganathan | G06N 3/0481 |
| 2020/0034998 A1* | 1/2020 | Schlemper | G01R 33/4824 |
| 2020/0082515 A1* | 3/2020 | Cardei | H04N 5/23229 |
| 2021/0192263 A1* | 6/2021 | Declerck | G16H 30/20 |

FOREIGN PATENT DOCUMENTS

| | | |
|---|---|---|
| CN | 107133461 A | 9/2017 |
| CN | 106373167 B | 10/2017 |

OTHER PUBLICATIONS

Schlemper, Jo, et al.; "A Deep Cascade of Convolutional Neural Networks for Dynamic MR Image Reconstruction", IEEE transactions on Medical Imaging, vol. 37, Issue: 2, pp. 491-503, Feb. 2018.
Zhu, Bo, et al.; "Image Reconstruction by Domain Transform Manifold Learning", Nature, vol. 555, pp. 487-492, Mar. 21, 2018.
Hyun, Chang Min, et al.; "Deep Learning for Undersampled MRI reconstruction", Physics in Medicine and Biology, vol. 63, Isuue: 13, Jun. 25, 2018.
Maglietta, Rosalia, et al.; "Random forest classification for hippocampal segmentation in 3D MR images", 2013 12th International Conference on Machine Learning and Applications; pp. 264-267.
Chang, Peter D., et al.; "Inception-CS: Deep Learning for Sparse MR Reconstruction in Glioma Patients", downloaded Apr. 21, 2022; pp. 1-4.

\* cited by examiner

SYSTEMS AND METHODS FOR PREDICTING OUTCOMES USING RAW DATA

CROSS-REFERENCE TO RELATED APPLICATION

This application claims priority to and the benefit of India Patent Application No. 201841048774, entitled "SYSTEMS AND METHODS FOR PREDICTING OUTCOMES USING RAW DATA", filed Dec. 22, 2018, which is herein incorporated by reference in its entirety.

BACKGROUND

The subject matter disclosed herein generally relates to image processing, and more particularly to systems and methods for predicting outcomes using only raw data.

Recently, machine learning techniques have been used extensively in the field of image processing and more particularly in the field of medical imaging, diagnostics, and analytics. In particular, medical imaging and/or analytics have immensely benefited by the infusion of deep learning techniques. Accordingly, these deep learning techniques have become an indispensable part of a solution chain in medical imaging and analytics. Use of deep learning algorithms have resulted in steep advancement of the state-of-the-art in many medical imaging tasks. Traditionally, acquired raw data corresponding to an object of interest is first processed to generate one or more reconstructed images. These reconstructed images are then employed to facilitate medical analytics such as diagnosis, treatment planning, and the like. There have also been recent advances that have accelerated or improved the reconstruction of medical images from raw data. It may be noted that a majority of the advancements have come from mapping the reconstructed medical images to clinical outcomes such as tumor segmentation, survival rate, pathology risk map, and the like. However, use of the currently available reconstruction techniques disadvantageously results in "information loss." This information loss in turn may adversely impact outcomes of interest.

BRIEF DESCRIPTION

Certain embodiments commensurate in scope with the originally claimed subject matter are summarized below. These embodiments are not intended to limit the scope of the claimed subject matter, but rather these embodiments are intended only to provide a brief summary of possible embodiments. Indeed, the invention may encompass a variety of forms that may be similar to or different from the embodiments set forth below.

In one embodiment, a processor-implemented method for generating a clinical output is provided. In accordance with this method, input raw data is acquired using an imaging system; a selection input corresponding to a clinical task is received; a task-specific model corresponding to the clinical task is retrieved; the raw data is mapped onto an application specific manifold using the task-specific model; the clinical output is generated based upon the mapping of the raw data onto the application specific manifold; and the clinical output for review is provided. Non-limiting examples of the clinical output may include segmentation, clinical detection, survival rate, therapy recommendation, and pathology risk. Segmentation may include image segmentation, volume segmentation, or any combination thereof to segment one or more organs for analyses. Diagnostic classification may include determining the presence of an abnormality in a given image or volume, determining the type of present abnormality, or any combination thereof. Clinical detection may include determining the presence of a tumor in a given image or volume. For example, clinical detection may involve determining whether a stroke is hyper-acute, acute, or sub-acute from a magnetic resonance (MR) image. Based on imaging characteristics of a lesion (e.g., glioblastoma) and variables such as location of lesion and blood report of patient, the survival rate of a the patient may be determined. For example, survival rates may be determined in situations involving drug trials. Moreover, a non-limiting example of therapy recommendation may include determining whether to inject a patient with tissue plasminogen activator (tpA) or perform a thrombectomy procedure. A non-limiting example of pathology risk may include determining the areas at risk from tissue damage as seen on magnetic resonance imaging (MRI) data in cases associated with mild traumatic brain injury.

In a further embodiment, an image data processing system is provided. In accordance with this embodiment, the image data processing system comprises a user interface; an acquisition or accessing subsystem configured to acquire or access raw image data; and a processing subsystem configured to receive a selection input from the user interface. The processing subsystem comprises a machine learning model corresponding to a task-specific model retrieved based upon the selection input; and a prediction platform configured to map the raw image data to the task-specific model to generate a clinical outcome. Non-limiting examples of the clinical outcome may be one of a binary value, multi-class value, multi-label (e.g., hyper-acute stroke), other categorical variables, and a continuous quantity value (e.g., age) corresponding to a classification or an image corresponding to a segmented region of interest.

In an additional embodiment, a method for generating a task-specific model for use in processing raw image data to generate a clinical outcome is provided. In accordance with this method, raw image data is received; an indication of a selected clinical task is received; one or more ground truth inputs corresponding to the raw image data and the selected clinical task are received; using the raw image data, the selected clinical task, and the one or more ground truth inputs, one or more model parameters are adjusted to conform one or more predicted outcomes with the one or more ground truth inputs; and an application specific manifold approximation is trained using the one or more model parameters to generate the task-specific model.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
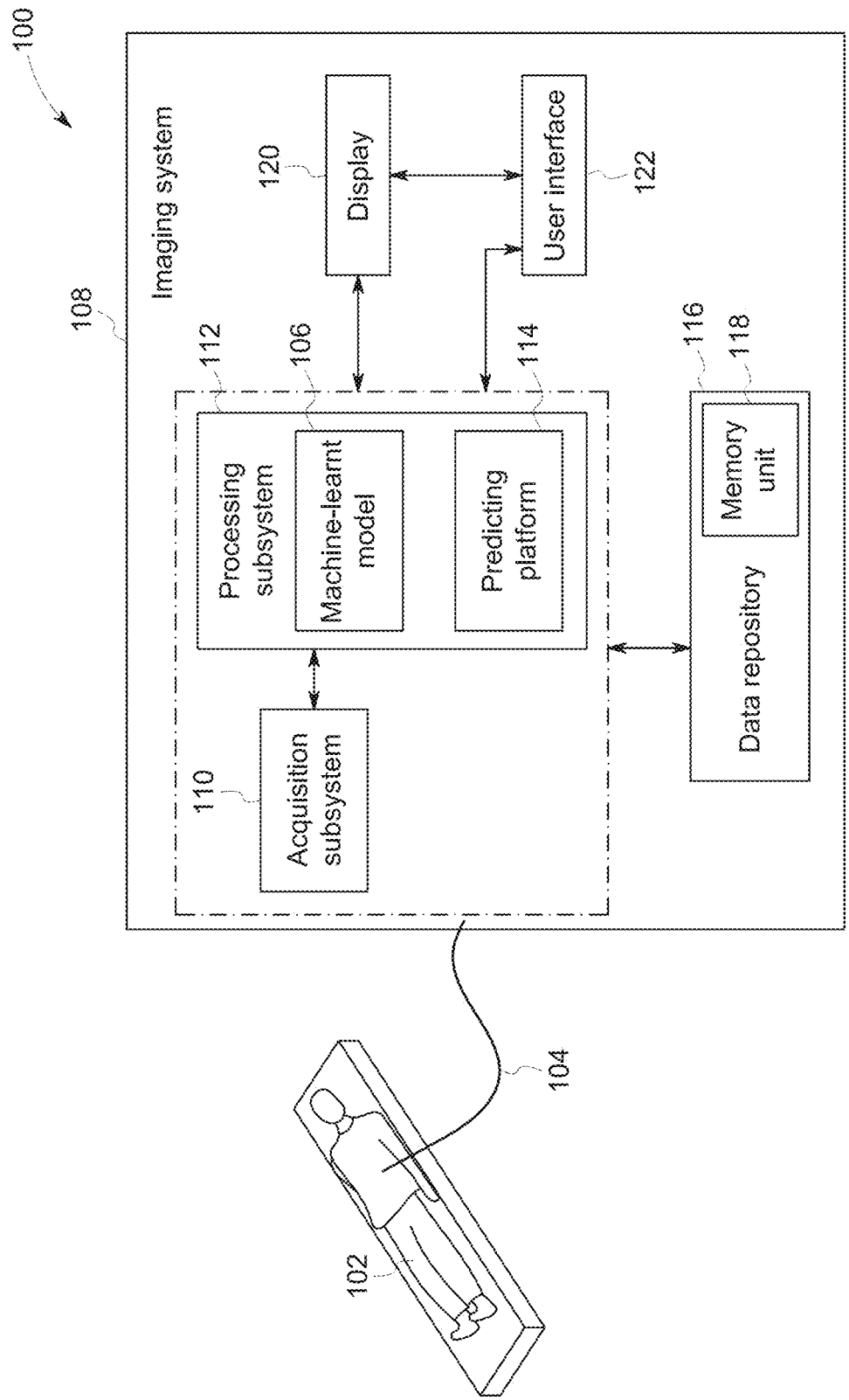
FIG. 1 is a schematic representation of an exemplary system for predicting outcomes using raw data, in accordance with aspects of the present specification.

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

The following description presents exemplary systems and methods for predicting outcomes using raw data. Particularly, embodiments described hereinafter present exemplary systems and methods that facilitate enhanced prediction of outcomes based only on the raw data to provide enhanced solutions. For example, the systems and methods facilitate enhanced performance of application specific tasks, thereby providing better clinical outcomes. In particular, the traditional reconstruction step is bypassed and raw data is directly mapped to clinical outcomes. Operating in raw data space presents significant advantages in reliably predicting quantitative measurements and/or other outcomes, thereby circumventing the drawbacks of currently available, traditional methods.

For clarity, exemplary embodiments of the present systems and methods are described in the context of a medical imaging system such as a magnetic resonance imaging (MRI) system. It may be noted that although the exemplary embodiments illustrated hereinafter are described in the context of a medical imaging system, other imaging systems and applications such as industrial imaging systems and non-destructive evaluation and inspection systems, such as pipeline inspection systems, liquid reactor inspection systems, are also contemplated. Some other examples of the medical imaging system may include a computed tomography (CT) system, a single photon emission computed tomography system (SPECT) system, a magnetoencephalography system (MEG), an Electrical impedance tomography (EIT), an X-ray imaging system, an optical imaging system, and/or an ultrasound imaging system. Additionally, the exemplary embodiments illustrated and described hereinafter may find application in multi-modality imaging systems that employ an MRI system in conjunction with other imaging modalities, position-tracking systems or other sensor systems. In one example, the multi-modality imaging system may include an MRI system and an X-ray imaging system. Furthermore, in other non-limiting examples of the multi-modality imaging systems, the MRI system may be used in conjunction with other imaging systems, such as, but not limited to, a computed tomography (CT) imaging system, a contrast enhanced ultrasound imaging system, an ultrasound imaging system, an optical imaging system, an X-ray imaging system and other imaging systems, in accordance with aspects of the present specification. An exemplary environment that is suitable for practicing various implementations of the present system and methods is discussed in the following sections with reference to FIG. 1.

FIG. 1 illustrates an exemplary imaging system 100 configured to receive and process raw data corresponding to a target volume in a subject 102 such as a patient or a non-biological object to generate an outcome, where the outcome is used for further diagnosis, analysis, follow-up and/or treatment planning. In particular, the system 100 is configured to use an exemplary technique to directly process raw data to generate a desired outcome such as a clinical outcome. In one embodiment, the imaging system 100 for example, may include an MRI system, an X-ray imaging system, a PET system, a SPECT system, a CT imaging system, a hybrid imaging system (e.g. MRI Elastography system or MR-PET or PET-CT system), and/or a multi-modality imaging system.

As used herein, the term "raw data" refers to data received directly from a data source. For example, the raw data may include sensor data received as is from a sensor or data received from a sensor and re-arranged for further tasks. Non-limiting examples of rearranging data include converting the data from a matrix to a single column vector and regridding the data (e.g., radial trajectory raw MRI kspace data regridded to Cartesian trajectory). Other non-limiting examples of raw data include data from various imaging systems and other types of sensors. Also, as used herein, the term "outcome" is used to refer to various tasks and information derived from them such as, but not limited to, segmentation, segmentation volume, classification, detection, survival rate, therapy decision, triaging of subjects, pathology risk map, and the like.

In one embodiment, the patient 102 may be suitably positioned, for example, on a table to allow the system 100 to image the target volume of the patient 102. During imaging, an image acquisition device 104 that is operatively coupled to a medical imaging system 108 may be used to acquire image data corresponding to an object or the target volume/region of interest in the patient 102.

Additionally, the medical imaging system 108 is configured to receive an input image or raw data corresponding to the patient 102 and process the raw data to generate an output such as a task specific outcome corresponding to the patient 102. In a presently contemplated configuration, the system 100 may be configured to acquire raw data representative of the patient 102. As noted hereinabove, in one embodiment, the system 100 may acquire image data corresponding to the patient 102 via the image acquisition device 104. Also, in one embodiment, the image acquisition device 104 may include a probe, where the probe may include an invasive probe, or a non-invasive or external probe, such as an external ultrasound probe, that is configured to aid in the acquisition of image data. Also, in certain other embodiments, image data may be acquired via one or more sensors (not shown) that may be disposed on the patient 102 or via use of other means of acquiring image data corresponding to the patient 102. By way of example, the sensors may include physiological sensors (not shown) such as positional sensors. In certain embodiments, the positional sensors may include electromagnetic field sensors or inertial sensors. These sensors may be operatively coupled to a data acquisition device, such as an imaging system, via leads (not shown), for example. Other methods of acquiring image data corresponding to the patient 102 are also contemplated.

Moreover, the medical imaging system 108 may include an acquisition subsystem 110 and a processing subsystem 112, in one embodiment. Further, the acquisition subsystem 110 of the medical imaging system 108 is configured to acquire raw data corresponding to a target region or region of interest in the patient 102 via the image acquisition device 104, in one embodiment. It may be noted that the terms image data, raw data, raw image data, and input image may be used interchangeably.

In addition, the acquisition subsystem 110 may also be configured to acquire images stored in an optical data storage article (not shown), which may be used to onto the application specific manifold. The application specific manifold will be described in more detail below. It may be noted that the optical data storage article may be an optical storage medium, such as a compact disc (CD), a digital versatile disc (DVD), multi-layer structures, such as DVD-5 or DVD-9, multi-sided structures, such as DVD-10 or DVD-18, a high definition digital versatile disc (HD-DVD), a Blu-ray disc, a near field optical storage disc, a holographic storage medium, or another like volumetric optical storage medium, such as, for example, two-photon or multi-photon absorption storage format. Further, the images so acquired by the acquisition subsystem 110 may be stored locally on the medical imaging system 108 in a data repository 116, for example.

Additionally, the raw data acquired from the patient 102 may then be processed by the processing subsystem 112. The processing subsystem 112, for example, may include one or more application specific processors, graphical processing units, digital signal processors, microcomputers, microcontrollers, Application Specific Integrated Circuits (ASICs), Field Programmable Gate Arrays (FPGAs), Programmable Logic Arrays (PLAs), and/or other suitable processing devices. Alternatively, the processing subsystem 112 may be configured to store the acquired raw data and/or user input in a data repository 116 and/or in a memory unit 118 for later use. In one embodiment, the data repository 116, for example, may include a hard disk drive, a floppy disk drive, a compact disk-read/write (CD-R/W) drive, a Digital Versatile Disc (DVD) drive, a flash drive, and/or a solid-state storage device.

It may be noted that the examples, demonstrations, and process steps that may be performed by certain components of the present system, for example by the processing subsystem 112, may be implemented by suitable code on a processor-based system. To that end, the processor-based system, for example, may include a general-purpose or a special-purpose computer. It may also be noted that different implementations of the present specification may perform some or all of the steps described herein in different orders or substantially concurrently.

According to aspects of the present specification, the raw data acquired and/or processed by the medical imaging system 108 may be employed to perform one or more tasks to facilitate generation of desired outcomes. In one example, the processing subsystem 112 may include a machine-learnt model 106 such as a neural network that is configured to aid in performing the tasks. In particular, the machine-learnt model 106 may be trained using a dataset such as raw data to generate one or more task specific model that are configured to perform corresponding tasks. The machine-learnt model 106 may also be referred to as a task specific model. By way of a non-limiting example, the machine-learnt model 106 may be trained to classify a new set of raw data or segment one or more regions such as a tumor in the new set of raw data to aid a clinician in providing a diagnosis. The machine-learnt model 106 may also be configured to perform other tasks such as, but not limited to, tumor segmentation, survival rate, pathology risk map, segmentation, classification, detection, triaging subject, therapy decision, and the like. In certain embodiments, the processing subsystem 112 may be further coupled to a storage system, such as the data repository 116, where the data repository 116 is configured to store the acquired image data. In certain embodiments, the data repository 116 may include a local database (not shown).

Moreover, in accordance with aspects of the present specification, the imaging system 100 may also include the memory unit 118. Although the configuration of FIG. 1 depicts the data repository 116 as including the memory unit 118, in other embodiments, the memory unit 118 may be a standalone unit that is external to the data repository 116 and/or the imaging system 100. The memory unit 118 is configured to store raw data, models 106, and outputs generated by the system 100.

As previously noted, some presently available techniques suffer from degraded performance of imaging systems due to loss of information during the reconstruction process, thereby adversely impacting outcomes of interest. In accordance with aspects of the present specification, the imaging system 100 is designed to circumvent such shortcomings. More particularly, imaging system 100 includes a predicting platform 114 that is configured to aid in the prediction of outcomes based directly on the received raw data. In particular, the predicting platform 114 obviates the need for the traditionally performed reconstruction step and/or any other processing steps that result in information loss. The exemplary system 100 that includes the predicting platform 114 provides a framework that bypasses the reconstruction step and directly maps raw data to clinical outcomes. More specifically, the system 100 and the predicting platform in particular operates in raw data space, thereby enhancing the prediction of quantitative measurements or outcomes, where traditional methods tend to fail. The predicting platform 114 works in conjunction with the machine-learnt model 106 to enhance the performance of the system 100

Also, in the presently contemplated configuration illustrated in FIG. 1, the processing subsystem 112 is shown as including the predicting platform 114. However, in certain embodiments, the predicting platform 114 may also be used as a standalone unit that is physically separate from the processing subsystem 112 and the medical imaging system 108. By way of example, the predicting platform 114 may be external to and operatively coupled to the medical imaging system 108.

In accordance with aspects of the present specification, a given model is trained to generate task specific outcomes. It is desirable that the machine-learnt model 106, when deployed, aids the predicting platform 114 in performing a specific task to generate a desired outcome. By way of example, the predicting platform 114 may be configured to use the machine-learnt model 106 in processing the acquired raw data to classify the raw data and/or segment one or more regions of interest in the raw data.

Accordingly, in operation, the predicting platform 114 and/or the machine-learnt model 106 are configured to receive the raw data, where the raw data corresponds to a task of interest in the patient 102. Further, the predicting platform 114 is also configured to receive input representative of a selected task. In certain embodiments, the input regarding the selected task may be provided by a user such as a clinician. Also, some non-limiting examples of the selected task include segmentation, classification, detection, and the like. By way of example, the selected task may entail segmenting the hippocampus region from raw data corresponding to the brain of the patient 102.

Additionally, the predicting platform 114 is configured to retrieve a model corresponding to the selected task. In certain embodiments, subsequent to receipt of the raw data and the selected task, the predicting platform 114 is configured to query the data repository 116 and/or the memory unit 118 to identify a corresponding model based on the selected task. In one example, if the selected task entails segmenting the hippocampus region using the raw data, the predicting platform 114 may query the data repository 116 to identify a model based on the selected task. In one embodiment, the predicting platform 114 is configured to retrieve the desired model from the data repository 116. In the present example, the machine-learnt model 106 is a model that is configured to perform the segmentation task. It may be noted that the memory unit 118 is configured to store the task specific models, raw data, and generated outcomes.

Subsequently, the predicting platform 114 is configured to perform application specific manifold approximation using the retrieved model. The retrieved machine learning model encompasses parameters that map the raw data onto a task specific representation. This application specific representation or manifold effectively infers a highly non-linear relationship which links the outcome to raw data. Following this step, the desired outcome(s) is/are generated. With continuing reference to the hippocampus segmentation example, the desired outcome may be a segmentation of the hippocampus region from the raw data.

It may be noted that the models corresponding to the specific tasks to be performed may be generated. In one example, the task specific models may be generated offline. In certain embodiments, raw data corresponding to a target region, one or more selected tasks, and corresponding ground truths may be received. An output configured to match or minimize loss between a prediction of an outcome and a corresponding ground truth is generated based on the received inputs. Moreover, an application specific manifold approximation may be learnt based on the generated output to generate a task specific model. These models are used to predict a clinical outcome using the raw data.

In addition, the predicting platform 114 is configured to provide the outcome to facilitate further analysis, diagnosis, and/or treatment planning. Also, the output generated may be based on the task performed by the machine-learnt model 106. For example, if the machine-learnt model 106 is configured to classify the input image, the output may be a binary value. However, if the machine-learnt model 106 is configured to segment the input image, the output may be an image corresponding to the segmented region(s) of interest. Moreover, in one example, the output may be visualized on an interface unit such as a display 120.

Furthermore, as illustrated in FIG. 1, the medical imaging system 108 may include the display 120 and a user interface 122. In certain embodiments, such as in a touch screen, the display 120 and the user interface 122 may overlap. Also, in some embodiments, the display 120 and the user interface 122 may include a common area. In accordance with aspects of the present specification, the display 120 of the medical imaging system 108 may be configured to display or present the outcome generated by the prediction platform 114. Moreover, any quality metrics/indicators generated by the predicting platform 114 may also be visualized on the display 120. In one example, the outcome and/or quality metrics/indicators may be superimposed on a reconstructed image to facilitate enhanced visualization.

In addition, the user interface 122 of the medical imaging system 108 may include a human interface device (not shown) configured to aid the clinician in manipulating image data displayed on the display 120. The human interface device may include a mouse-type device, a trackball, a joystick, a stylus, or a touch screen configured to facilitate the clinician to identify the one or more regions of interest in the images. However, as will be appreciated, other human interface devices, such as, but not limited to, a touch screen, may also be employed. Furthermore, in accordance with aspects of the present specification, the user interface 122 may be configured to aid the clinician in navigating through the acquired images and/or output generated by the medical imaging system 108. Additionally, the user interface 122 may also be configured to aid in manipulating and/or organizing the displayed images and/or generated indicators displayed on the display 120.

Implementing the imaging system 100 that includes the prediction platform 114 as described hereinabove aids in enhancing the performance of the imaging system 100 by generating clinically relevant outcomes directly from the raw data, while obviating the need for reconstruction steps.

Figure 2:
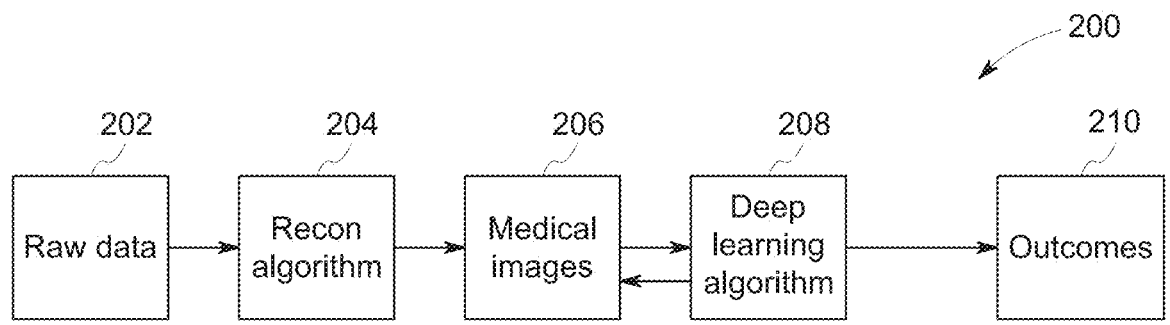
FIG. 2 is a schematic representation of a currently available method for predicting outcomes.

FIG. 2 is a schematic illustration 200 of a currently available, traditional medical imaging workflow. As depicted in FIG. 2, raw data 202 is received by an imaging system (not shown in FIG. 2) and processed by a reconstruction technique 204 to generate one or more medical images 206. Subsequently, these reconstructed images 206 are processed by a deep learning technique 208 to generate outcomes 210. However, the reconstruction step 204 is a computationally intensive process. Also, the reconstruction step 204 may result in loss of information, thereby leading to degradation in the generated outcomes. For example, image reconstruction steps are typically lossy transformation steps due to numerous imaging filters and numerical compromises used to generate a clinically acceptable image. In particular, in modalities such as MRI where the data is complex having real and imaginary components, the conventional reconstruction process typically generates the magnitude data for clinical interpretation and report generation and discards the phase information.

In accordance with exemplary aspects of the present specification, the systems and methods described herein entail generating clinically relevant outcomes by directly mapping raw data. The working of the system 100 (see FIG.

1) and the predicting platform 114 (see FIG. 1) in particular may be better understood with reference to the exemplary logic depicted in FIGS. 3-7.

In the present specification, embodiments of exemplary methods of FIGS. 3-7 may be described in a general context of computer executable instructions on a computing system or a processor. Generally, computer executable instructions may include routines, programs, objects, components, data structures, procedures, modules, functions, and the like that perform particular functions or implement particular abstract data types.

Additionally, embodiments of the exemplary methods of FIGS. 3-7 may also be practiced in a distributed computing environment where optimization functions are performed by remote processing devices that are linked through a wired and/or wireless communication network. In the distributed computing environment, the computer executable instructions may be located in both local and remote computer storage media, including memory storage devices.

Further, in FIGS. 3-7, the exemplary methods are illustrated as a collection of blocks in a logical flow chart, which represents operations that may be implemented in hardware, software, or combinations thereof. The various operations are depicted in the blocks to illustrate the functions that are performed. In the context of software, the blocks represent computer instructions that, when executed by one or more processing subsystems, perform the recited operations.

The order in which the exemplary methods of FIGS. 3-7 are described is not intended to be construed as a limitation, and any number of the described blocks may be combined in any order to implement the exemplary methods disclosed herein, or equivalent alternative methods. Additionally, certain blocks may be deleted from the exemplary methods or augmented by additional blocks with added functionality without departing from the spirit and scope of the subject matter described herein. Although, the exemplary embodiments illustrated hereinafter are described in the context of a medical imaging system, it will be appreciated that use of the systems and methods in industrial applications is also contemplated in conjunction with the present specification.

Figure 3:
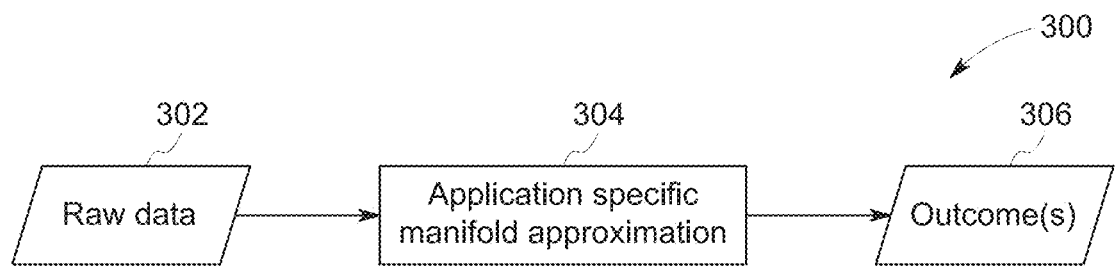
FIG. 3 is a schematic representation illustrating an exemplary method for predicting outcomes using raw data, in accordance with aspects of the present specification.

Referring now to FIG. 3, a schematic illustration 300 of an exemplary method for predicting outcomes using raw data is presented. The method 300 of FIG. 3 is described with reference to the components of FIG. 1. In one embodiment, the method 300 may be performed by the predicting platform 114 in conjunction with the machine-learnt model 106.

The method 300 includes receiving raw data 302, when the imaging system 100 and the machine-learnt model 106 in particular is deployed. The raw data 302 corresponds to a target region of interest in a subject such as the patient 102. Also, the raw data 302 may be received by the machine-learnt model 106 and the predicting platform 114. Further, the raw data 302 may undergo pre-processing, such as a Fourier transform, prior to being mapped to the application specific manifold.

Further, at step 304, an application specific manifold approximation is performed using the raw data to generate a desired outcome 306. As noted hereinabove, a machine-learnt model such as the task specific model 106 may be used to process the raw data to generate the desired outcome. The models may be generated offline and stored in the data repository 116.

Figure 4:
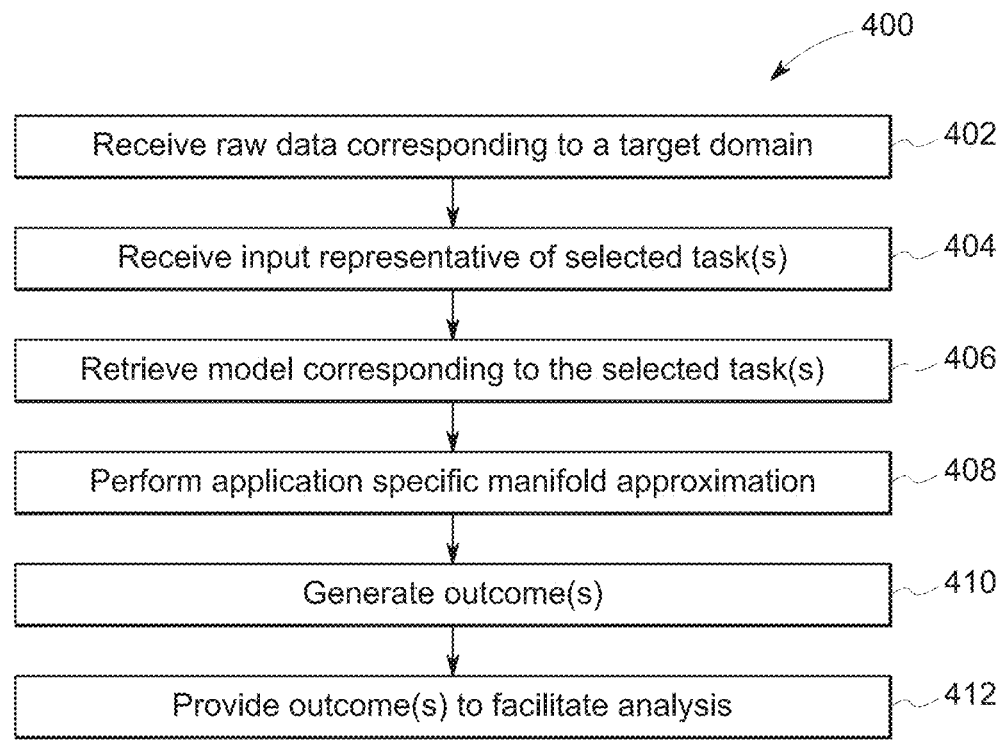
FIG. 4 is a flow chart illustrating a method for predicting outcomes using raw data, in accordance with aspects of the present specification.

Turning now to FIG. 4, a flow chart 400 depicting an exemplary method for predicting outcomes using raw data is presented. The method 400 of FIG. 4 is described with reference to the components of FIG. 1. In one embodiment, the method 400 may be performed by the predicting platform 114 in conjunction with the machine-learnt model 106.

The method starts at step 402, where raw data is received. The raw data may correspond to a target region of interest in the patient 102. By way of example, the raw data may correspond to the brain region of the patient 102. Subsequently, at step 402, an input representative of one or more selected tasks may be received. As previously noted, the task may include a segmentation, a classification, a detection, and the like. Also, in one embodiment, the input corresponding to the selected tasks may be provided by a user such as a clinician. In certain other embodiments, the input may be provided via automated means. By way of example, the clinician may provide an input indicating that it is desirable to segment the hippocampus region in the brain. Moreover, as indicated by step 406, a model corresponding to the selected task may be retrieved. In one embodiment, the desired task specific model may be retrieved from the data repository 116 based on the selected task.

Subsequent to the receipt of the raw data, the selected task, and the corresponding model, an application specific manifold approximation may be performed, as depicted in step 408. Additionally, prior to being mapped to the application specific manifold (i.e., as part of a pre-processing step), the raw data may undergo a Fourier transform. The model converts and projects the raw data onto an application specific manifold. The application specific manifold may be a learnt non-linear relationship that maps raw data and outcomes encoded as model parameters.

Consequent to the processing of the raw data by the corresponding model, one or more desired outcomes may be generated, as indicated by step 410. More particularly, the outcome generated by predicting platform 114 may vary based on the task performed by the machine-learnt model 106. By way of example, if the machine-learnt model 106 is used to perform a classification task, the outcome generated may be a categorical value. In a similar fashion, if the machine-learnt model 106 is used to perform a segmentation task, the outcome generated may be a mask or a segmented image. In one example, the desired outcome may be the segmented hippocampus region.

Furthermore, the generated outcome may be utilized to facilitate further analysis, diagnosis, triaging, or treatment planning, as indicated by step 412. By way of example, the predicting platform 114 may be configured to visualize the mask or segmented image and/or the categorical values generated by the machine-learnt model 106 on the display 120. Additionally, any metrics associated with the generated outcome may also be visualized on the display 120. In certain embodiments, the metrics and/or the segmented image may be superimposed on a corresponding reconstructed image on the display 120.

In another example, the predicting platform 114 may also be configured to communicate the generated output to a user such as a clinician or another system. The clinician and/or another system may use the output to facilitate a diagnosis and/or an analysis.

As noted hereinabove, one or more task specific models are employed to facilitate directly mapping raw data to generate clinically relevant outcomes. These models may be generated offline, in certain embodiments and stored in the data repository 116.

Figure 5:
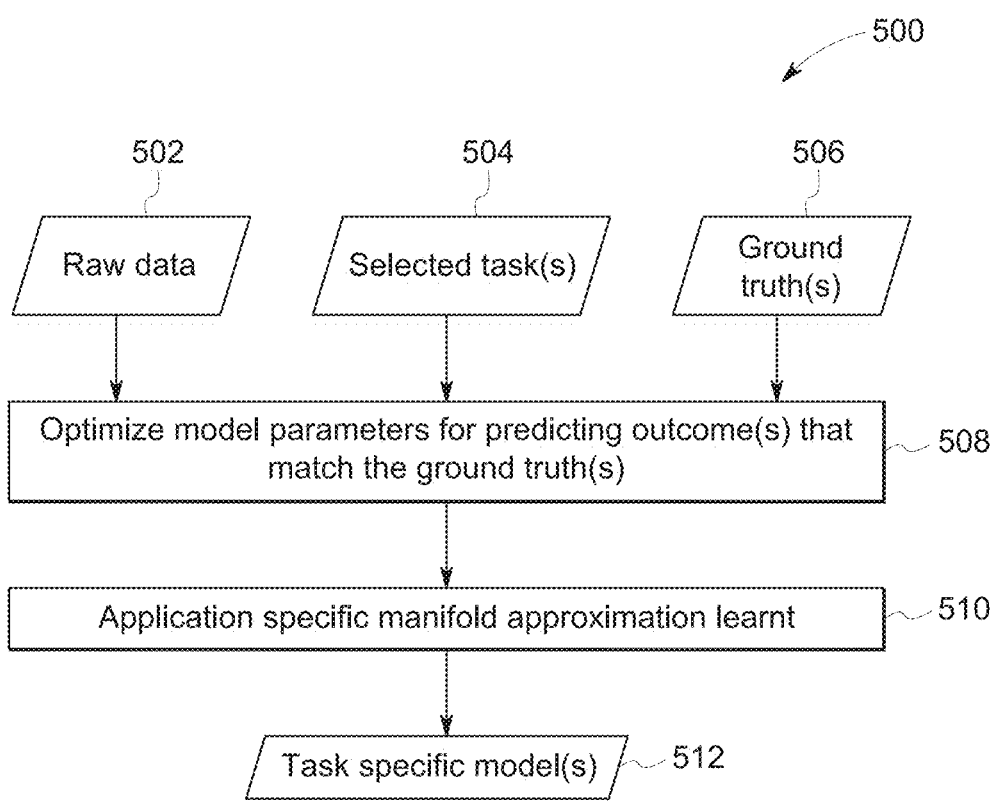
FIG. 5 is a flow chart illustrating a method for generating models for use in the method for predicting outcomes using raw data of FIG. 4, in accordance with aspects of the present specification.

FIG. 5 presents a flow chart 500 depicting one method of generating a task specific model. Also, FIG. 5 is described with reference to the components of FIGS. 1 and 3-4.

The method 500 begins by receiving as input raw data 502, one or more selected tasks 504, and ground truths 506.

Further, at step 508, one or more outputs are generated. More particularly, these outputs are generated such that loss between the prediction(s) and the ground truth(s) are minimized or ensure that the prediction(s) match closely with the ground truth(s). Subsequently, application specific manifold approximation is learnt, as indicated by step 510 to generate one or more task specific models 512. The learnt manifold approximation encompasses a mapping function for the highly non-linear relationship between the outcome and raw data. This mapping function is encoded as parameters of the machine learning model. By way of example, if the selected task is a segmentation, then the task specific model 512 is configured to facilitate generation of a mask or a segmented region directly from the raw data. It may be noted, that the task specific model 512 may be configured to perform a single task or a plurality of tasks.

Figure 6:
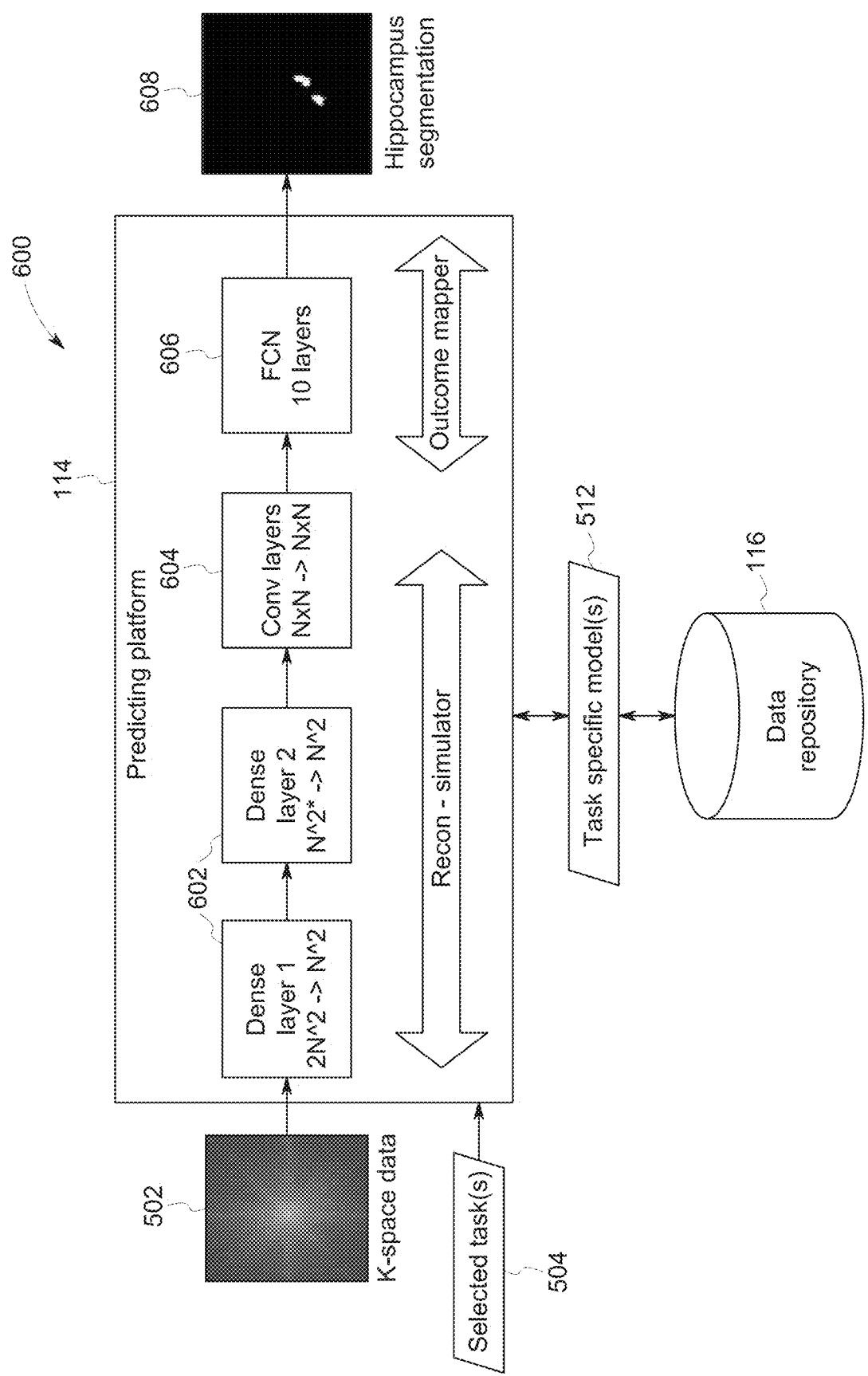
FIG. 6 is a schematic illustration of a deep learning architecture for use in the method for predicting outcomes using raw data of FIG. 5, in accordance with aspects of the present specification.

Referring now to FIG. 6, a schematic illustration 600 of the method 500 for predicting outcomes from raw data, in accordance with aspects of the present specification, is presented. FIG. 6 is described with reference to the components of FIGS. 1 and 3-5.

Raw data 502 is acquired and provided to the predicting platform 114. In one example, the raw data may be MRI data organized as Cartesian k-space data. Also, inputs corresponding to the selected tasks 504 may be provided to the predicting platform 114. Based on the selected tasks, the predicting platform 114 may retrieve one or more task specific models 512 from the data repository 116.

One embodiment of the predicting platform 114 is presented in FIG. 6. The predicting platform 114 may include one or more dense layers 602 and convolutional layers 604. The dense layers 602 are configured to perform linear combinations of layer inputs and layer weights followed by non-linear operation such as, but not limited to, sigmoid or hyperbolic tangent functions. Also, the convolutional layers 604 are configured to perform series of convolution, normalization, and regularization operations on the layer inputs with kernel weights followed by non-linear functions mentioned above. Additionally, the predicting platform 114 includes fully convolutional network (FCN) layers 606, which are configured to perform the segmentation tasks from the previous layers input. Consequent to processing of the raw data 502 using the task specific models 512, a desired outcome 608 is generated. In the example of FIG. 6, the raw data 502 may correspond to the brain of the patient 102 and the selected task 504 may include segmentation of the hippocampus region. Accordingly, the desired outcome 608 is a segmented hippocampus.

Figure 7A:
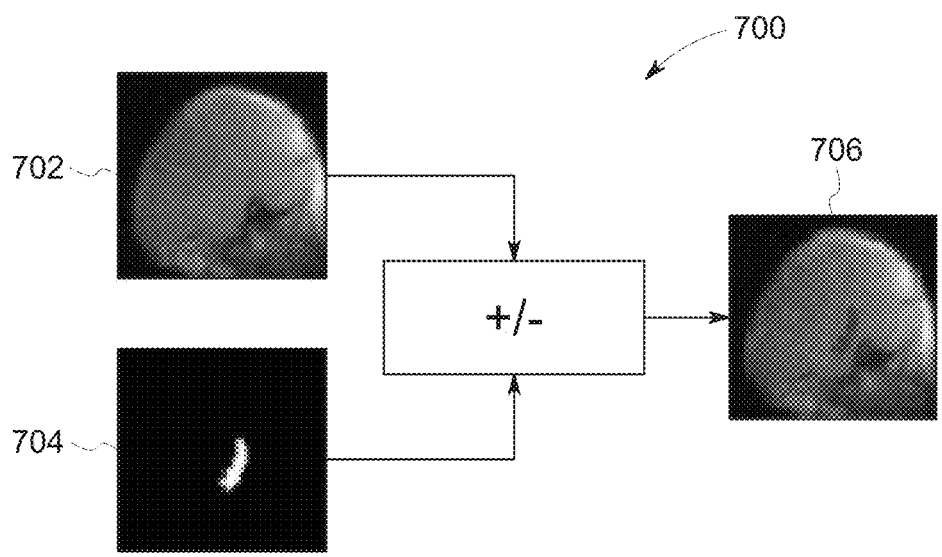
FIGS. 7(a), 7(b), and 7(c) are schematic illustrations of a comparison of performance of a currently available technique and the method for predicting outcomes using raw data of FIG. 5, in accordance with aspects of the present specification.
Figure 7B:
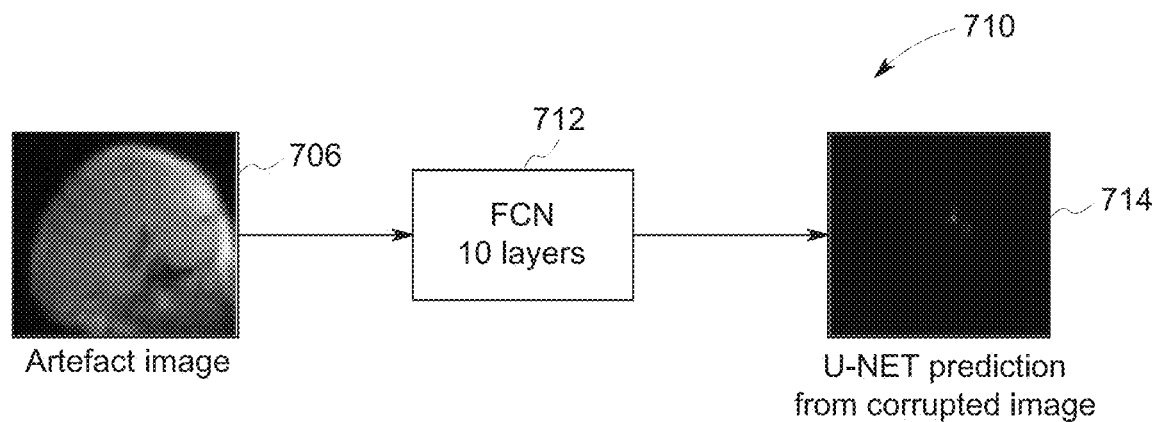
Figure 7C:
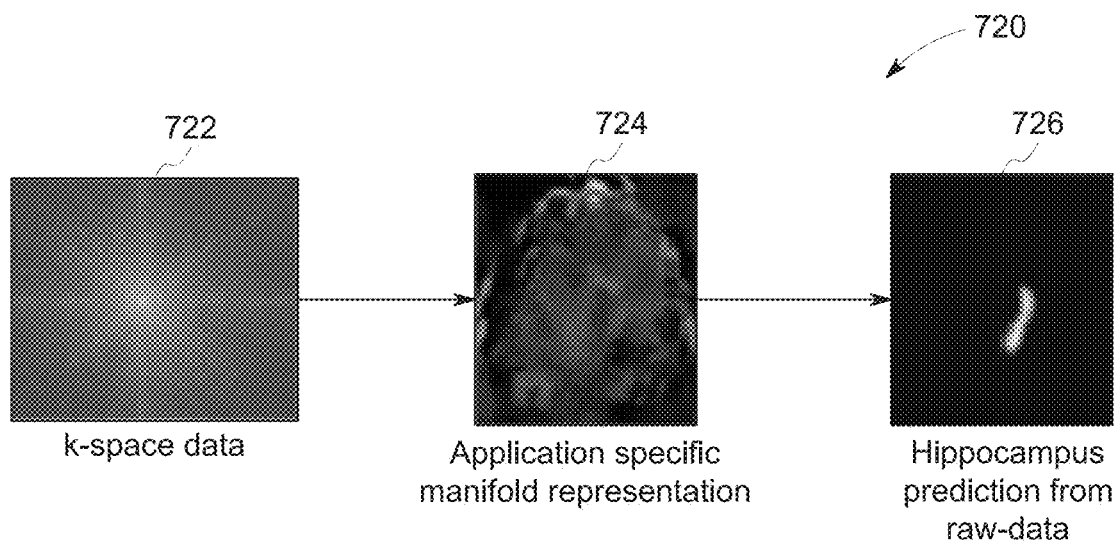

Turning now to FIGS. 7(a)-7(c), diagrammatical representations of a comparison of performance of a conventional imaging technique and the method for predicting outcomes using raw data of FIG. 5 in segmenting a region of interest are presented. Also, FIGS. 7(a)-7(c) are described with reference to the components of FIGS. 1 and 3-6.

In the example depicted in FIGS. 7(a), a schematic illustration 700 of an artifact simulator set up is presented. In particular, an extreme case of an artifact 704 is introduced in an image 702 to generate an artifact simulated image 706. The artifact image 706 has the artificially introduced artifact 704. More specifically, a region of interest in the image 702 is modified by a determined percentage of maximum dynamic range. In one example, the region of interest may be eroded by about 10% of the maximum dynamic range.

FIGS. 7(b) and 7(c) present a comparison of performance of predicting a hippocampus segmentation. In particular, FIG. 7(b) presents a schematic representation 710 of a method of predicting a hippocampus segmentation from the image domain using a currently available technique such as a U-Net 712. The U-Net 712 may be a deep learning neural network such as a convolutional neural network developed for image segmentation and image analysis. In particular, the artifact simulated image 706 is processed by the U-Net 712 to provide an outcome 714.

FIG. 7(c) is a schematic representation 720 of the method of predicting the hippocampus segmentation directly from raw data 722 using the exemplary predicting platform 114. The raw data 722 may be k-space data from the artifact simulated image 706, in one example. Also, reference numeral 724 refers to an intermediate representation using the k-space data from the artifact simulated image 706. The raw data 722 is directly mapped to generate an outcome 726 such as the segmented hippocampus.

As clearly depicted in FIGS. 7(b) and 7(c), predicting the hippocampus from the raw data 722 of a corrupted image such as the artifact simulated image 706, results in a more faithful reproduction of the desired outcome such as hippocampus maps 726. However, traditional image-based segmentation fails in predicting the hippocampus from a corrupted image such as the artifact simulated image 706.

Figure 8:
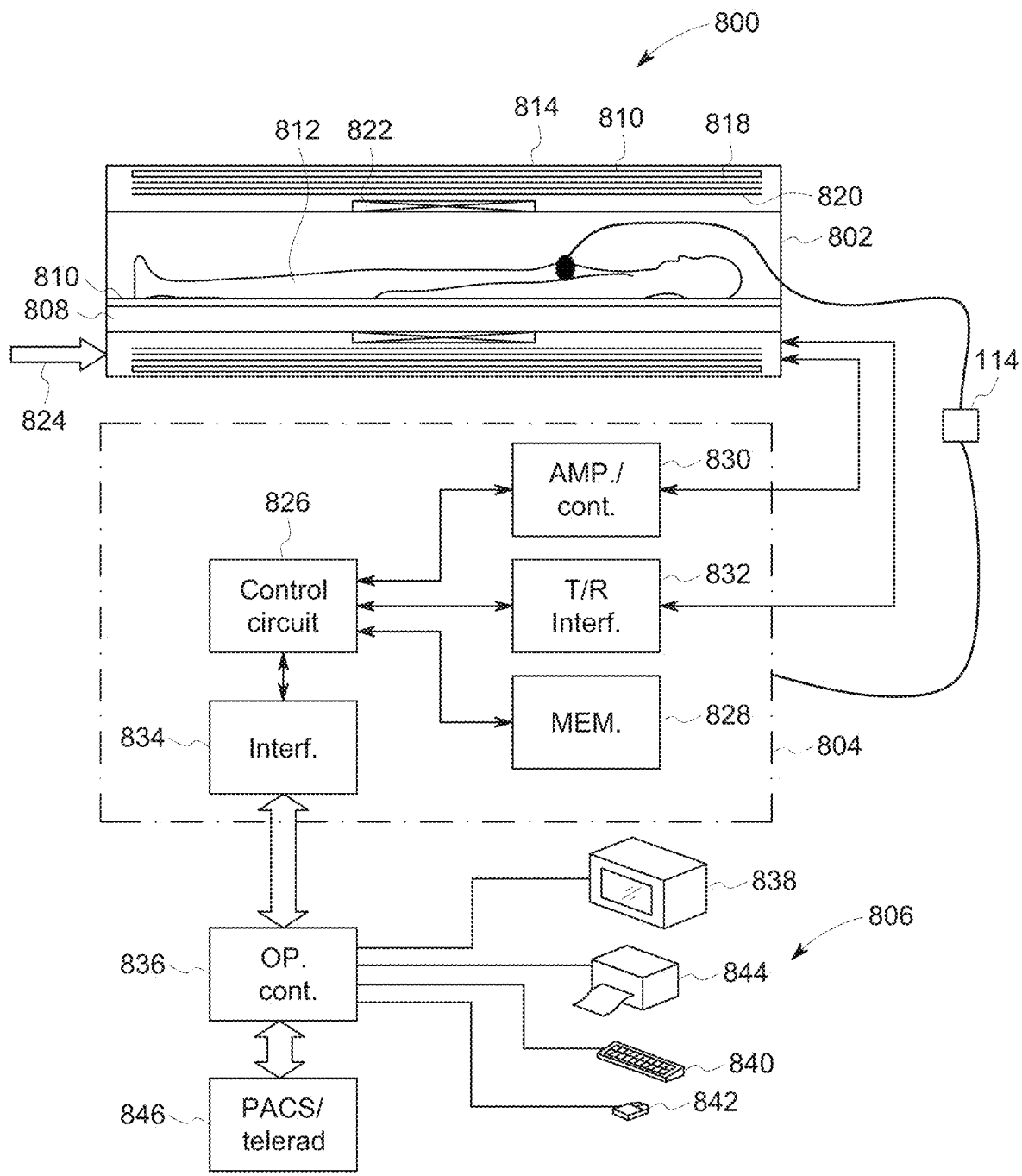
FIG. 8 is a diagrammatical representation of magnetic resonance imaging system for use in the system of FIG. 1, in accordance with aspects of the present specification.

As noted with reference to FIG. 1, the medical imaging system 108 may be an MRI system. FIG. 8 presents one embodiment 800 of an MRI system.

FIG. 8 is a block diagram of an embodiment of an MRI system 800. The MRI system 800 is illustrated diagrammatically as including a scanner 802, scanner control circuitry 804, and system control circuitry 806. While the MRI system 800 may include any suitable MRI scanner or detector, in the illustrated embodiment the system includes a full body scanner including a patient bore 808 into which a table 810 may be positioned to place a patient 812, such as the patient 102 in a desired position for scanning. The scanner 802 may be of any suitable type of rating, including scanners varying from 0.5 Tesla ratings to 3 Tesla ratings and beyond.

Additionally, the scanner 802 may include a series of associated coils for producing controlled magnetic fields, for generating radio-frequency (RF) excitation pulses, and for detecting emissions from gyromagnetic material within the patient 812 in response to such pulses. In the diagrammatical view of FIG. 8, a primary magnet coil 814 may be provided for generating a primary magnetic field generally aligned with patient bore 808. A series of gradient coils 816, 818 and 820 may be grouped in a coil assembly for generating controlled magnetic gradient fields during examination sequences as will be described in greater detail hereinafter. A RF coil 822 may be provided for generating radio frequency pulses for exciting the gyromagnetic material. In the embodiment illustrated in FIG. 8, the coil 822 also serves as a receiving coil. Thus, the RF coil 822 may be coupled with driving and receiving circuitry in passive and active modes for receiving emissions from the gyromagnetic material and for applying RF excitation pulses, respectively. Alternatively, various configurations of receiving coils may be provided separate from the RF coil 822. Such coils may include structures specifically adapted for target anatomies, such as head coil assemblies, and so forth. Moreover, receiving coils may be provided in any suitable physical configuration, including phased array coils, and so forth.

In a presently contemplated configuration, the gradient coils 816, 818 and 820 may have different physical configurations adapted to their function in the imaging system 800. As will be appreciated by those skilled in the art, the coils include conductive wires, bars or plates that are wound or cut to form a coil structure that generates a gradient field upon application of control pulses as described below. The placement of the coils within the gradient coil assembly may be done in several different orders. In one embodiment, a Z-axis coil may be positioned at an innermost location, and may be formed generally as a solenoid-like structure that has relatively little impact on the RF magnetic field. Thus, in the illustrated embodiment, the gradient coil 820 is the Z-axis solenoid coil, while the coils 816 and 818 are Y-axis and X-axis coils respectively.

The coils of the scanner 802 may be controlled by external circuitry to generate desired fields and pulses, and to read signals from the gyromagnetic material in a controlled manner. As will be appreciated by those skilled in the art, when the material, typically bound in tissues of the patient, is subjected to the primary field, individual magnetic moments of the paramagnetic nuclei in the tissue partially align with the field. While a net magnetic moment is produced in the direction of the polarizing field, the randomly oriented components of the moment in a perpendicular plane generally cancel one another. During an examination sequence, an RF frequency pulse is generated at or near the Larmor frequency of the material of interest, resulting in rotation of the net aligned moment to produce a net transverse magnetic moment. This transverse magnetic moment precesses around the main magnetic field direction, emitting RF signals that are detected by the scanner 802 and processed for reconstruction of the desired image.

The gradient coils 816, 818 and 820 may be configured to serve to generate precisely controlled magnetic fields, the strength of which vary over a predefined field of view, typically with positive and negative polarity. When each coil is energized with known electric current, the resulting magnetic field gradient is superimposed over the primary field and produces a desirably linear variation in the Z-axis component of the magnetic field strength across the field of view. The field varies linearly in one direction, but is homogenous in the other two. The three coils have mutually orthogonal axes for the direction of their variation, enabling a linear field gradient to be imposed in an arbitrary direction with an appropriate combination of the three gradient coils.

The pulsed gradient fields perform various functions integral to the imaging process. Some of these functions are slice selection, frequency encoding and phase encoding. These functions may be applied along the X-axis, Y-axis and Z-axis of the original coordinate system or along other axes determined by combinations of pulsed currents applied to the individual field coils.

The slice select gradient determines a slab of tissue or anatomy to be imaged in the patient. The slice select gradient field may be applied simultaneously with a frequency selective RF pulse to excite a known volume of spins within a desired slice that precess at the same frequency. The slice thickness is determined by the bandwidth of the RF pulse and the gradient strength across the field of view.

The frequency encoding gradient is also known as the readout gradient, and is usually applied in a direction perpendicular to the slice select gradient. In general, the frequency encoding gradient is applied before and during the formation of the magnetic resonance (MR) echo signal resulting from the RF excitation. Spins of the gyromagnetic material under the influence of this gradient are frequency encoded according to their spatial position along the gradient field. By Fourier transformation, acquired signals may be analyzed to identify their location in the selected slice by virtue of the frequency encoding.

The phase encode gradient is generally applied before the readout gradient and after the slice select gradient. Localization of spins in the gyromagnetic material in the phase encode direction may be accomplished by sequentially inducing variations in phase of the precessing protons of the material using slightly different gradient amplitudes that are sequentially applied during the data acquisition sequence. The phase encode gradient permits phase differences to be created among the spins of the material in accordance with their position in the phase encode direction.

As will be appreciated by those skilled in the art, a great number of variations may be devised for pulse sequences employing the exemplary gradient pulse functions described hereinabove as well as other gradient pulse functions not explicitly described here. Moreover, adaptations in the pulse sequences may be made to appropriately orient both the selected slice and the frequency and phase encoding to excite the desired material and to acquire resulting MR signals for processing.

The coils of the scanner 802 are controlled by scanner control circuitry 804 to generate the desired magnetic field and RF pulses. In the diagrammatical view of FIG. 8, the control circuitry 804 thus includes a control circuit 826 for commanding the pulse sequences employed during the examinations, and for processing received signals. The control circuit 826 may include any suitable programmable logic device, such as a CPU or digital signal processor of a general purpose or application specific computer. Also, the control circuit 826 may further include memory circuitry 828, such as volatile and non-volatile memory devices for storing physical and logical axis configuration parameters, examination pulse sequence descriptions, acquired image data, programming routines, and so forth, used during the examination sequences implemented by the scanner.

Interface between the control circuit 826 and the coils of the scanner 802 is managed by amplification and control circuitry 830 and by transmission and receive interface circuitry 832. The amplification and control circuitry 830 includes amplifiers for each gradient field coil to supply drive current to the field coils in response to control signals from control circuit 826. Transmit/receive (T/R) circuitry 832 includes additional amplification circuitry for driving the RF coil 822. Moreover, where the RF coil 822 serves both to emit the RF excitation pulses and to receive MR signals, the T/R circuitry 832 may typically include a switching device for toggling the RF coil between active or transmitting mode, and passive or receiving mode. A power supply, denoted generally by reference numeral 824 in FIG. 8, is provided for energizing the primary magnet 814. Finally, the scanner control circuitry 804 may include interface components 834 for exchanging configuration and image data with system control circuitry 806. It should be noted that, while in the present description reference is made to a horizontal cylindrical bore imaging system employing a superconducting primary field magnet assembly, the present technique may be applied to various other configurations, such as scanners employing vertical fields generated by superconducting magnets, permanent magnets, electromagnets or combinations of these means.

The system control circuitry 806 may include a wide range of devices for facilitating interface between an operator or radiologist and the scanner 802 via the scanner control circuitry 804. In the illustrated embodiment, for example, an operator controller 836 is provided in the form of a computer workstation employing a general purpose or application specific computer. The workstation also typically includes memory circuitry for storing examination pulse sequence descriptions, examination protocols, user and patient data, image data, both raw and processed, and so forth. Further, the workstation may further include various interface and peripheral drivers for receiving and exchanging data with local and remote devices. In the illustrated embodiment, such devices include a conventional computer keyboard 840 and an alternative input device such as a mouse 842. A printer 844 may be provided for generating hard copy output of documents and images reconstructed from the acquired data. Moreover, a computer monitor 838 may be provided for facilitating operator interface. In addition, the system 800 may include various local and remote image access and examination control devices, represented generally by reference numeral 846 in FIG. 8. Such devices may include picture archiving and communication systems, teleradiology systems, and the like.

The aforementioned components may be dedicated hardware elements such as circuit boards with digital signal processors or may be software running on a general-purpose computer or processor such as a commercial, off-the-shelf personal computer (PC). The various components may be combined or separated according to various embodiments of the invention. Thus, those skilled in the art will appreciate that the present MRI system 800 is provided by way of example, and the present specification is in no way limited by the specific system configuration.

In the example of FIG. 8, an exemplary predicting platform such as the predicting platform 114 of FIG. 1 is shown as being operatively coupled to the MRI system 800. However, in certain other embodiments, the predicting platform 114 may be an integral part of the MRI system 800.

Furthermore, the foregoing examples, demonstrations, and process steps such as those that may be performed by the system may be implemented by suitable code on a processor-based system, such as a general-purpose or special-purpose computer. It should also be noted that different implementations of the present specification may perform some or all of the steps described herein in different orders or substantially concurrently, that is, in parallel. Furthermore, the functions may be implemented in a variety of programming languages, including but not limited to C++, Python or Java. Such code may be stored or adapted for storage on one or more tangible, machine readable media, such as on data repository chips, local or remote hard disks, optical disks (that is, CDs or DVDs), memory or other media, which may be accessed by a processor-based system to execute the stored code. Note that the tangible media may include paper or another suitable medium upon which the instructions are printed. For instance, the instructions may be electronically captured via optical scanning of the paper or other medium, then compiled, interpreted or otherwise processed in a suitable manner if necessary, and then stored in the data repository or memory.

Embodiments of the present systems and methods for predicting outcomes from machine data advantageously present a technique to predict outcomes directly from raw data instead of operating in the image space. The systems and methods disclosed herein as operating in the raw data space provide significant advantages in reliably predicting the quantitative measurements or outcomes and are resistant to distortions occurring in imaging such as tissue distortion due to blooming artifacts.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A processor-implemented method for generating a clinical output, comprising:
    receiving as an input, raw data acquired using an imaging system;
    receiving a selection input corresponding to a clinical task;
    retrieving a task-specific model corresponding to the clinical task;
    mapping the raw data onto an application specific manifold using the task-specific model;
    generating the clinical output based upon the mapping of the raw data onto the application specific manifold, wherein the clinical output comprises an image segmentation; and
    displaying the clinical output via a display.

2. The processor-implemented method of claim 1, wherein the raw data is not reconstructed to generate an image as part of generating the clinical output.

3. The processor-implemented method of claim 1, wherein the raw data comprises data acquired directly from the imaging system.

4. The processor-implemented method of claim 3, wherein the raw data undergoes pre-processing prior to being mapped to the application specific manifold but is not reconstructed to image space.

5. The processor-implemented method of claim 1, wherein the clinical output further comprises one of a volume segmentation, a diagnostic classification, a clinical detection, a survival rate estimation, a therapy recommendation, a triaging recommendation, or a pathology risk map.

6. The processor-implemented method of claim 1, wherein the clinical output is one of a binary value, a categorical variable, or a continuous quantity value corresponding to a classification or an image corresponding to a segmented region of interest.

7. The processor-implemented method of claim 1, wherein the task- specific model is retrieved from a data repository based on the selection input.

8. The processor-implemented method of claim 1, wherein mapping the raw data onto the application specific manifold comprises converting and projecting the raw data onto the application specific manifold.

9. The processor-implemented method of claim 1, wherein the application specific manifold comprises a learned non-linear relationship that maps the raw data and clinical outputs encoded as parameters of the task-specific model.

10. The processor-implemented method of claim 1, wherein the raw data comprises Cartesian k-space data.

11. The processor-implemented method of claim 1, wherein the raw data undergoes a Fourier transform, prior to being mapped to the application specific manifold.

12. The processor-implemented method of claim 1, wherein the task-specific model is configured to facilitate generation of a mask or a segmented region directly from the raw data.

13. An image data processing system, comprising:
    a user interface;
    an acquisition or accessing subsystem configured to acquire or access raw image data;

a processing subsystem configured to receive a selection input from the user interface, the processing subsystem comprising:

a machine learning model corresponding to a task-specific model retrieved based upon the selection input; and a prediction platform configured to map the raw image data to the task-specific model to generate a clinical outcome, wherein the clinical outcome comprises an image segmentation.

14. The image data processing system of claim 13, wherein the machine learning model comprises a neural network.

15. The image data processing system of claim 13, wherein the task-specific model is retrieved from a data repository in response to the selection input.

16. The image data processing system of claim 13, wherein the machine learning model, when in use, infers a non-linear relationship linking the raw image data to the clinical outcome.

17. The image data processing system of claim 13, wherein the clinical outcome is one of a binary value, corresponding to a classification or an image corresponding to a segmented region of interest.

18. The image data processing system of claim 13, wherein the prediction platform maps the raw image data to the task-specific model to generate the clinical outcome by performing the steps of:

mapping the raw data onto an application specific manifold using the task-specific model; and generating the clinical outcome based upon the mapping of the raw image data onto the application specific manifold.

19. The image data processing system of claim 13, wherein the predicting platform comprises:

one or more dense layers configured to perform at least linear combinations of layer inputs and layer weights;

one or more convolutional layers configured to perform at least series of convolution, normalization, and regularization operations on an output of the one or more dense layers; and one or more fully convolutional network layers configured to perform segmentation tasks on a second output of the one or more convolutional layers.

20. A method for generating a task-specific model for use in processing raw image data to generate a clinical outcome, comprising:

receiving raw image data;

receiving an indication of a selected clinical task;

receiving one or more ground truth inputs corresponding to the raw image data and the selected clinical task;

using the raw image data, the selected clinical task, and the one or more ground truth inputs, adjusting one or more model parameters to conform one or more predicted outcomes with the one or more ground truth inputs; and training an application specific manifold approximation using the one or more model parameters to generate the task-specific model, wherein the application specific manifold approximation, when trained, is configured to map the raw image data to the task-specific model to generate the clinical outcome, wherein the clinical outcome comprises an image segmentation.

21. The method of claim 20, wherein adjusting the one or more model parameters to conform the one or more predicted outcomes with the one or more ground truth inputs comprises minimizing the differences between the one or more predicted outcomes and the one or more ground truth inputs.

22. The method of claim 20, wherein the application specific manifold approximation, when trained, comprises a mapping function for a non-linear relationship between the clinical outcome and the raw image data.

23. The method of claim 22, wherein the mapping function is encoded as parameters of a machine learning model.

* * * * *